United States Patent [19]

Nonomura

[11] Patent Number: Plant 6,169

[45] Date of Patent: May 3, 1988

[54] *BOTRYOCOCCUS BRAUNII* VAR. SHOWA

[75] Inventor: Arthur M. Nonomura, Del Mar, Calif.

[73] Assignee: The Regents of the University of CA, Berkeley, Calif.

[21] Appl. No.: 852,048

[22] Filed: Apr. 15, 1986

[51] Int. Cl.[4] ..... A01H 13/00

[52] U.S. Cl. ..... Plt./89

[58] Field of Search ..... Plt./89

*Primary Examiner*—Robert E. Bagwill

*Attorney, Agent, or Firm*—Townsend & Townsend

[57] ABSTRACT

*Botryococcus braunii* var. showa is chemotaxonomically distinct from previously cultured strains of the species in quality and quantity of hydrocarbons produced in vitro. Morphological and cultural differences distinguish this variety from other cultured strains of *Botryococcus braunii.* In particular, the variety is characterized by the ability to produce and secrete large amounts of botryococcenes during all phases of its growth cycle.

2 Drawing Sheets

The present invention is a new and distinct variety of alga of the *Botryococcus braunii* species designated by the varietal name "Showa." This new variety belongs to the Division Chlorophyta, Order Chlorococcales, and is maintained at the Laboratory of Chemical Biodynamics, Lawrence Berkeley Laboratory, University of California, Berkeley, Calif. 94720. A dried type specimen is available from the herbarium at the University of California, having accession UC147504.

The variety was originally isolated in June, 1980 from lily-culturing tanks located in a greenhouse located on the fifth floor of the Life Sciences Building of the University of California, Berkeley, Calif., 94720, by the following method. Whole soil water extract (Stein (Ed.) 1973, *Handbook of Phycological Methods,* Cambridge University Press, Great Britain, p. 448) was steam sterilized and then buffered to pH 7 with phosphate. The soil extract was supplemented with Provasoli's Enrichment Medium (Stein, supra.) at one-fourth normal strength and with an equal volume of 1 μm sterile filtered lily-culture water. Two thousand sterile disposable test tubes (12×75 mm) with friction fit plastic caps were each filled with 1.5 ml of the medium.

Floating orange colonies were collected from the lily pond culture water. Without washing, the colonies were diluted in an equal volume of sterile enriched culture medium. An aliquot of the algal culture was placed in a small sterile petri dish from which single colonies were selected by micropipette. Orange colonies were selected by means of an inverted microscope at low-power magnification (40×). Selected colonies were placed in the previously prepared test tubes containing enrichment medium. Single colony selection was confirmed by viewing the test tube through a dissecting microscope.

The test tubes were placed in plastic bags which were deflated and then filled with 50% carbon dioxide:50% nitrogen gas. The cultures were placed under 150 $\mu E/m^{-2}s^{-1}$ cool-white fluorescent illumination at 30° C. Cultures were continuously illuminated. When numerous colonies were observed in the tubes, additional medium was added. Within two weeks, cultures that were contaminated were removed. Approximately 200 unialgal cultures resulted from the 2000 single colony cultures that were started originally. One culture that was tested contained high levels of botryococcenes. This culture was named the Showa variety.

Maintenance cultures of the Showa variety were asexually reproduced by growth in semi-continuous culture at 22°-24° in 2.8 L Fernbach flasks continuously bubbled with air and illuminated with cool-white fluorescent tubes (125 $\mu E/m^{-2}s^{-1}$) on a 16:8 LD cycle. The standard defined growth medium contained the following components (mg/1 $H_2O$): $Ca(NO_3)_2.4H_2O$ (26.5), $MgSO_4.7H_2O$ (25), $K_2HPO_4$ (10), $H_3BO_3$ (0.6), MOPS buffer (3.14), $Na_2EDTA$ (7.7), $ZnCl_2$ (0.624), $CuCl_2.2H_2O$ (0.268), $NaMoO_4.2H_2O$ (0.252), $CoCl_2.6H_2O$ (0.420), $FeCl_3.6H_2O$ (2.5), and $MnCl_2.4H_2O$ (0.360). The nitrogen-supplemented medium (3N) contained three times the standard amount of combined nitrogen, while the media deficient in nitrogen (1/10-N) and phosphate (1/10-P) contained one-tenth the standard concentration of these components. Additional nitrate in the 3N medium was provided as $KNO_3$, whereas the $Ca^{+2}$ deleted in the 1/10-N medium was compensated for via the addition of $CaCl_2$. The pH of these media was adjusted to 6.5 with KOH before autoclaving.

The variety of the present invention is characterized by a high yield of particular branched hydrocarbons ($C_nH_{2n-10}$, n=30–37) referred to as botryococcenes. In contrast to previously identified varieties, the variety of the present invention is capable of rapid growth, with a mass doubling time of 40 hours or less under optimum conditions, resulting in a botryococcene yield equal to approximately 30% of the dry weight of the biomass. As the variety also secretes or sheds the botryococcenes from the colonial matrix, the variety is suited for the production of botryococcene hydrocarbons by continuous culture without the need to destroy the alga for hydrocarbon recovery. The botryococcenes are useful as a starting material for a number of hydrocarbon based products, such as fuels and petrochemicals.

DETAILED DESCRIPTION OF THE NEW VARIETY

Colonies of the Showa variety of *Botryococcus braunii* are various hues of green, yellow, orange or brown depending on the light regime or the physiological state of the culture. All color designations are made with reference to the Munsell Book of Color. Normal healthy colonies are 2.5 Y $\frac{7}{8}$ on the Munsell color chart. The colonies float at the surface of still cultures. They are indefinite in shape, range from 25 to 600 μm and consist of one to several irregular to spherical aggregates of cells. The colonies of cells are held together by a matrix that is rich in hydrocarbons. Rapidly growing colonies are peanut-shaped, being composed of two approximately spherical subunits. In slow-growing colonies in old cultures, multiple-colony aggregates of irregular shape are common:

Cells composing the colonies are 10–30 μm long and are ovoid, cuneate, pyriform or irregular in shape. They are individually embedded in matrix cups that comprise cell wall components and layers of hydrocarbon. Hydrocarbon deposits are components and layers of hydrocarbon. Hydrocarbon deposits are present intracellularly, in the matrix and on the surface of the colonies. The cell wall is thick, composed of an inner polysaccharide layer and a thin outer trilamellar structure. Cells contain a nucleus, one anteriorly located dictyosome and a cup-shaped chloroplast with a basal pyrenoid. No unusual organelles are present. Deposits of hydrocarbon 0.5 to 2.0 μm in diameter are present in the cytoplasm and in the wall and matrix. Binary fission is the only form of reproduction. A new matrix cup is formed around each cell following cytokinesis. Fragmentation causes propagation of the colonies.

Colonies grow in nutrient-enriched fresh to slightly brackish water under continuous or periodic (e.g., 16:8 h LD) light. They are tolerant of high light intensities (e.g., 150–250 $\mu E/m^{-2}s^{-1}$).

Figure 1:
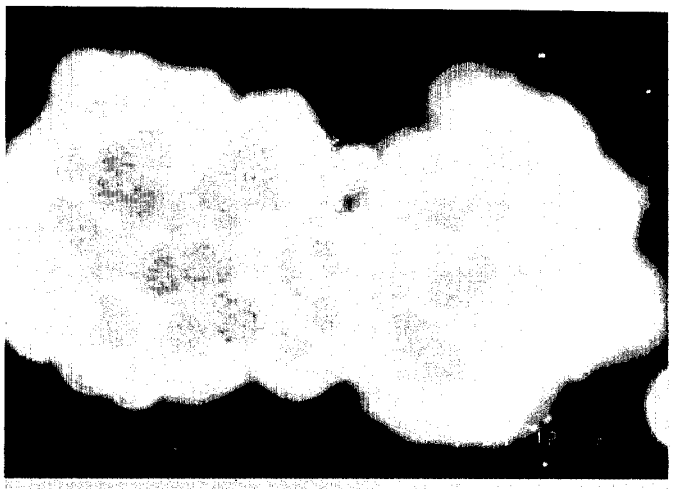
FIG. 1 is a photograph of the Showa variety of *Botryococcus braunii* consisting of an aggregate of two generally spherical colonies shown at 500× magnification.
Figure 2:
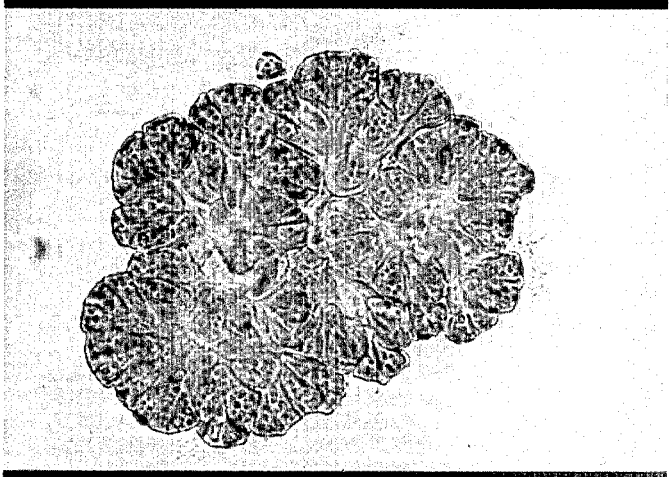
FIG. 2 is a photograph of a single generally spherical colony of the variety of the present invention taken with bright field optics showing the true colors.
Figure 3:
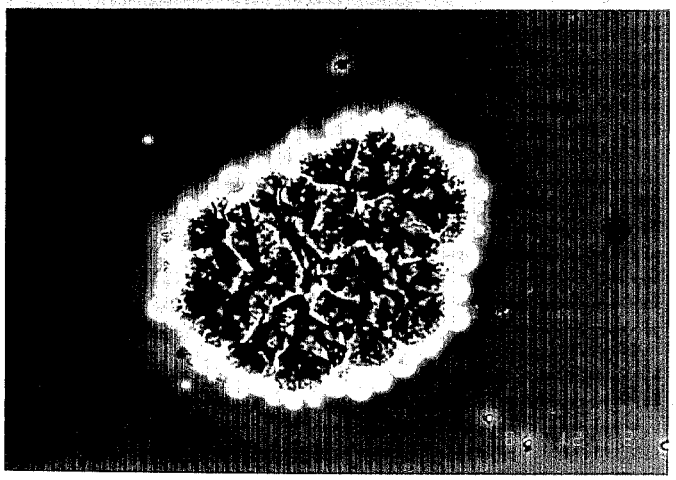
FIG. 3 is a photograph of a single generally spherical colony of the variety of the present invention taken with phase contrast optics showing oil droplets secreted by the alga.
Figure 4:
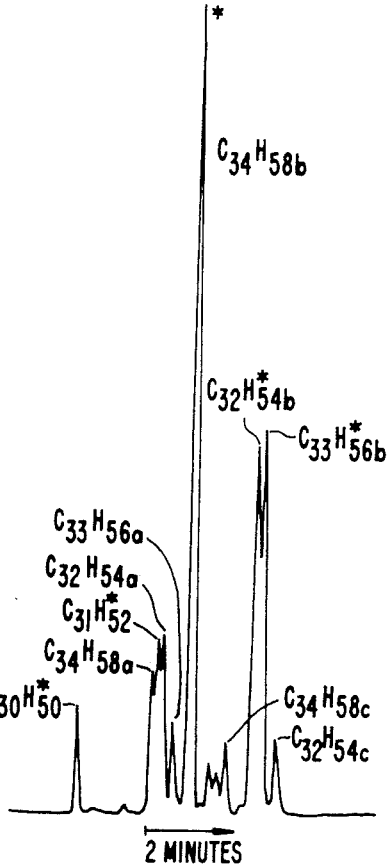
FIG. 4 is a GLC chromatogram of the botryococcene produced by the variety of the present invention, revealing a unique peak.
Figure 5A:
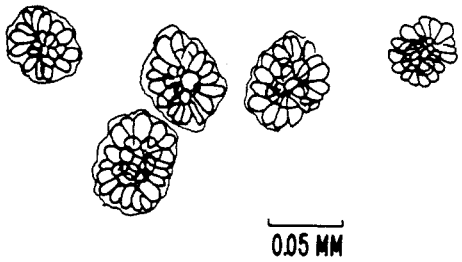
FIGS. 5A and 5B are line drawings of the variety of the present invention.
Figure 5B:
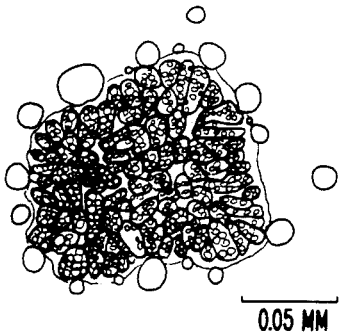

The new variety differs from typical *Botryococcus braunii* (e.g., the isolates available from the Cambridge Culture Collection) in colony structure and biochemistry. Colonies in typical *B. braunii* are more or less flat and composed of cells that are arranged radiately in a single layer towards the periphery, whereas, those of the new variety are globular with cells arranged in multiple layers. The new variety produces more botryococcene hydrocarbons (30% or more of dry weight) than the typical *B. braunii* (1.5 to 20%). The hydrocarbons produced by the new variety are distinctive, showing the $C_{32}H_{54}$ compound with a terminal $C_6$ ring in the last peak of the gas liquid chromatograph shown in FIG. 4. Physiologically, the new variety is distinguished from other strains by its rapid metabolism of nutrient carbon into hydrocarbons during active growth.

Defined growth medium for the strains of the present invention will usually include the following components in water. The pH will be adjusted to the range from 6.5 to 7.5, usually about 7.0, by the addition of acid or base.

Growth Medium

| Component | Concentration |
|---|---|
| $Ca(NO_3)_2.4H_2O$ | 50–250 mg/L |
| $NH_4Cl$ or $NH_4HCO_3$ | 10–150 mg/L |
| $MgSO_4.7H_2O$ | 10–100 mg/L |
| $K_2HPO_4$ or $KH_2PO_4$ | 0–50 mg/L |
| $H_3BO_3$ | 0–1 mg/L |
| $Na_2EDTA$ | 0–25 mg/L |
| $ZnCl_2$ | 0–10 μg/L |
| $CaCl_2.2H_2O$ | 0–10 mg/L |
| $NaMoO_4.2H_2O$ | 0–10 μg/L |
| $CoCl_2.6H_2O$ | 0–10 μg/L |
| $FeCl_3.6H_2O$ | 0–10 mg/L |
| $MnCl_2.4H_2O$ | 0–10 μg/L |
| $CuCl_2.2H_2O$ | 0–10 μg/L |

What is claimed is:

1. A new and distinct variety of algal plant having the characteristics described and illustrated herein.

* * * * *